(12) United States Patent
Cruz

(10) Patent No.: US 9,358,591 B2
(45) Date of Patent: Jun. 7, 2016

(54) METHOD AND DEVICE FOR CLEANING BREATHING HOSES

(71) Applicant: Isaac Cruz, Marina, CA (US)

(72) Inventor: Isaac Cruz, Marina, CA (US)

( * ) Notice: Subject to any disclaimer, the term of this patent is extended or adjusted under 35 U.S.C. 154(b) by 245 days.

(21) Appl. No.: 14/015,209

(22) Filed: Aug. 30, 2013

(65) Prior Publication Data

US 2015/0059805 A1 Mar. 5, 2015

(51) Int. Cl.
*B08B 9/043* (2006.01)
*A61M 16/08* (2006.01)

(52) U.S. Cl.
CPC .......... *B08B 9/0436* (2013.01); *A61M 16/0875* (2013.01); *A61M 2209/10* (2013.01)

(58) Field of Classification Search
CPC ........ B08B 9/0436; B08B 9/043; B08B 9/04; A47K 11/10; F41A 29/02
USPC ............................... 15/104.05, 104.16; 42/95
See application file for complete search history.

(56) References Cited

U.S. PATENT DOCUMENTS

| 214,484 | A | * | 4/1879 | Brown | F41A 29/02 15/104.18 |
| 2,537,149 | A | * | 1/1951 | McKean | A47L 17/00 15/104.16 |
| 2,798,238 | A | * | 7/1957 | Rogovin | F41A 29/02 15/104.16 |
| 2007/0266610 | A1 | * | 11/2007 | Coffield, III | F41A 29/02 42/95 |

* cited by examiner

*Primary Examiner* — Laura C Guidotti
(74) *Attorney, Agent, or Firm* — Peninsula IP Group; Douglas Chaikin

(57) ABSTRACT

Disclosed herein is a method and a device for cleaning an open airway ended tube. The tube being designed for attachment to a continuous positive airway apparatus. The device includes a cleaning element for cleaning the inside of the open ended tube and a support member. The cleaning element attached to the support member. The support member including means for attaching the cleaning element to the support member and for retaining the cleaning element to the support member during cleaning. Additionally, one end of the support member capable of being secured during cleaning.

4 Claims, 5 Drawing Sheets

METHOD AND DEVICE FOR CLEANING BREATHING HOSES

FIELD OF THE INVENTION

This invention relates to a device for cleaning air hoses and more particularly to an open ended airway tube designed to be attached to a continuous positive airway apparatus, such as a respirator and similar devices.

TECHNICAL BACKGROUND

The use of respirators and similar breathing apparatus have become a regular part of life for many. In addition to those needing respirators and similar devices for a medical condition, such asthma and emphysema, new strategies for healing illnesses are being developed that use oxygen therapy. Oxygen therapy relies heavily on such breathing apparatus because the cost of a hyperbaric chamber is prohibitive for most folks.

The breathing apparatus is referred to herein as a continuous positive airway apparatus CPAP. This apparatus develops a concentrated oxygenated air stream within the apparatus using the environmental air. The CPAP apparatus includes an output. Connected to the output of the CPAP is a hose or an airway tube. The subject of this invention is the cleaning of the airway tube.

Typically manufacturers of such tubular airways recommend cleaning with the use of a mild soap. The mild soap is mixed with water and then applied to the internal surfaces of the tube to wash away any contaminants. Typically, the soapy water is swished about the inside of the tube and the tube rinsed off and left to air dry.

As readily apparent, this kind of method may be at least somewhat inefficient and very time consuming. Additionally, after repeated usage soap residue builds up on the interior walls of the tube and degrade the tube. Additionally, the water left to its own device does not completely dry before the user is ready for its next use. The user is then left with a wet hose or additional waiting time.

What is needed is a method and device for thoroughly and efficiently cleaning the airway tube.

SUMMARY OF THE INVENTION

Accordingly to overcome the above mentioned disadvantages of the known devices and to solve the long felt needs in the art, it is a general object of the instant invention to provide a kit and a method for using the kit to efficiently and effectively clean hoses intended for use with CPAP apparatus.

It is an additional object of the method and kit of the instant invention to provide a device, which is easily assembled and easy to use to efficiently and effectively clean such hoses.

It is an additional object of the method in accordance with this invention, which enables a user to simply and effectively clean open ended airway tubes.

In accordance with the objects set forth above and as will be described more fully below, the device for cleaning an airway hose, defining an open ended tube, the airway hose specifically adapted for attachment to a continuous positive airway apparatus, in accordance with this invention, comprises:

a cleaning member for cleaning the inside of the open ended tube;
a support member, the cleaning element attached to the support member, the support member including means for attaching the cleaning element to the support member and for retaining the cleaning element to the support member during cleaning;
and
one end of the support member capable of being fixed during cleaning.

In an exemplary embodiment, the cleaning element comprises a cotton swab having a central opening and is replaceably attached to the support member.

In another exemplary embodiment, the support member is made from a nylon-like material, which provides enough rigidity to be threaded through the central opening of the cleaning element.

In another exemplary embodiment in accordance with this invention, the method of using the device according to the invention comprises the steps of:

supplying a support member having proximal and distal ends and a cleaning member;
attaching the cleaning member to the support member such that the cleaning member is in close proximity to the proximal end;
inserting the distal end of the support member through the open ended airway tube;
securing the distal end of the support member; and
pulling open ended airway tube over the cleaning member.

It is an advantage of the device and method of the invention to provide a kit which enables the user to efficiently and effectively clean tubing intended for use with a CPAP.

It is an additional advantage of the device and method of the invention to provide an economical and readily usable kit which enables the user to efficiently and effectively clean tubing intended for use with a CPAP.

BRIEF DESCRIPTION OF THE DRAWING

For a further understanding of the objects and advantages of the present invention, reference should be made to the following detailed description, taken in conjunction with the accompanying drawing, in which like parts are given like reference numerals and wherein.

DETAILED DESCRIPTION OF THE INVENTION

In order to appreciate the invention herein, one must appreciate the need in the art as set forth in the Background and the objects and advantages as described in the Summary of the Invention, above. Most importantly, the structure of the instant invention herein resolves the long felt need to provide the user of a CPAP apparatus with a method and device for efficiently and effectively cleaning the airway supply hose.

Figure 1:
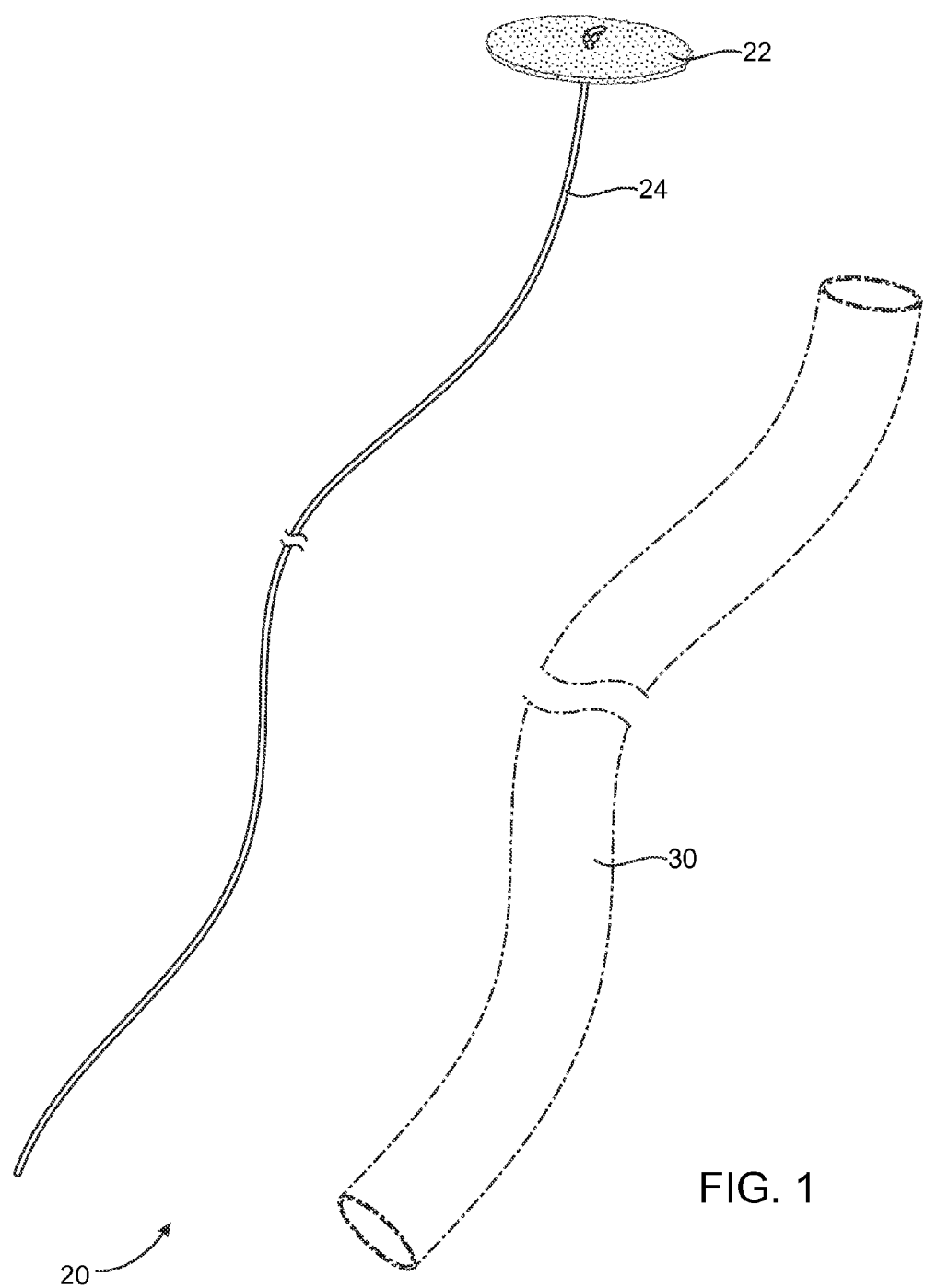
FIG. 1 is a plan view illustrating an exemplary embodiment of the cleaning device in accordance with this invention ready for use.

With particular reference to FIG. 1, there is shown the structure of invention, generally indicated by the numeral 20. The exemplary embodiment of instant invention shown in FIG. 1 includes a cleaning element 22 and a support member 24. As shown particularly in FIG. 2, the cleaning element 22 has a central opening 26 providing the means for attaching the cleaning element 22 to the support member 24.

Figure 3:
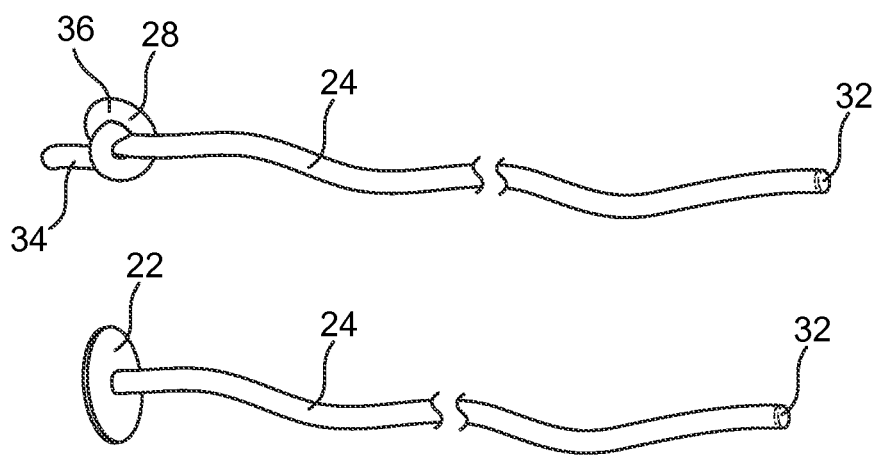
FIG. 3 is a plan view of an exemplary embodiment of the support member and support member with the cleaning element in accordance with this invention.

As shown in FIG. 3, the support member 24 includes a retaining member 28 as a means for retaining the cleaning member 22 on the support member 24. As will be explained in more detail below, the exemplary embodiment of the retaining member comprises the proximal end of the support member 24 being turned into a knot and fixed in position.

As illustrated in FIG. 1, in an exemplary embodiment of the structure in accordance with the invention, the support member 24 and the airway supply hoses have predetermined lengths. As illustrated, the support member 24 is a length somewhat greater than the length of the airway supply hose.

The airway supply hose, once removed from the CPAP defines an open ended tube 30 in the exemplary embodiment shown in FIG. 1. The tube 30 attaches one end to the CPAP apparatus (not shown) and the other end to the user interface. Typically, a face mask (not shown) provides the user interface.

As noted above, FIG. 2 illustrates in detail the cleaning element 22 having central opening 26. The cleaning element 22 is attached to the support member 24 by threading distal end of the support member 24 through the central opening 26 as clearly illustrated in FIGS. 1 & 3.

Figure 2:
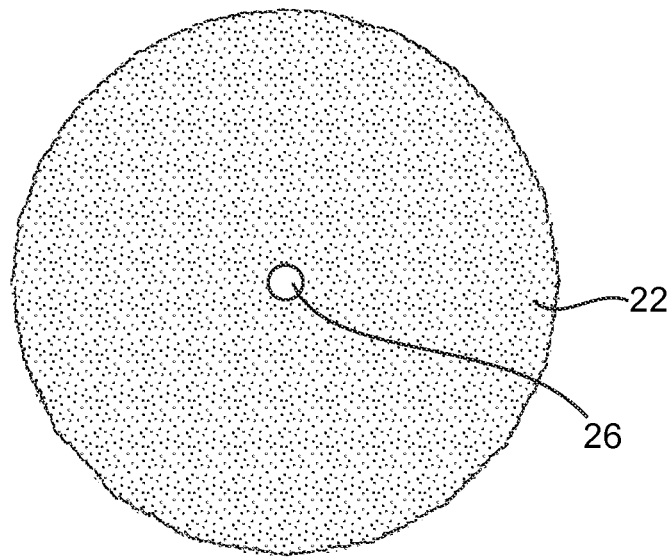
FIG. 2 is a plan view of the cleaning element.

In the exemplary embodiment of the invention shown in FIG. 2, the cleaning member 22 comprises a cotton swab having predetermined diameter. The predetermined diameter slightly larger, but compatible with the internal diameter of the tube 30 so that during use the interior surfaces of the tube are thoroughly contacted as will be explained more fully below.

FIG. 3, illustrates in detail, the support member 24 with and without the cleaning member 22 attached. The support member 24 has a first end, defining a distal end 32 and a second end, defining a proximal end 34. The distal end 32 is threaded through the central opening 26 of the cleaning member 22. The proximal end 34 includes structure for retaining the cleaning member 22 on the support member defining a retaining member 36.

In the exemplary embodiment, the support member 24 defines a rope-like chord of nylon mesh. The distal end 32 is singed to provide a structure which eases the access of the support member 24 through the central opening 26. In further exemplary embodiments, the distal end 32 is shaped and molded into a pointed end further easing the entry of the support member 24 through the central opening 26. The singed end of the distal end 32 provides additional rigidity to facilitate the insertion of the distal end 32 through the opening 26.

The proximal end 34, in the exemplary embodiment shown in FIG. 3, is formed into a knot as shown. The knot is heat treated, singed again, as with the distal end 32. The heat treatment fixes the knot and thus defines a member 36 for retaining the cleaning member 22 on the support member 24 during cleaning.

IN USE

Figure 4:
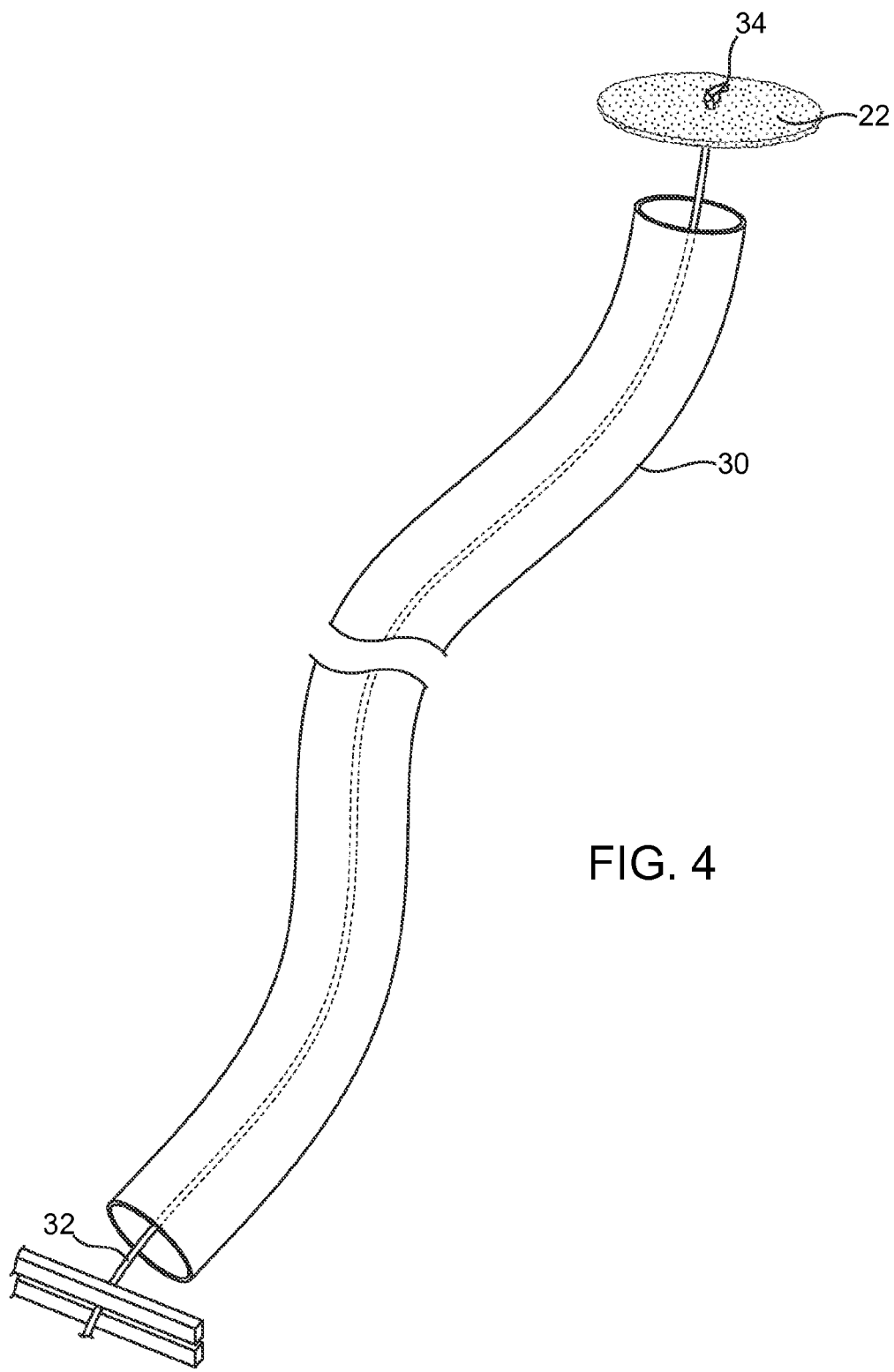
FIGS. 4 & 5 illustrate an exemplary embodiment of the cleaning device in accordance with this invention in use.
Figure 5:
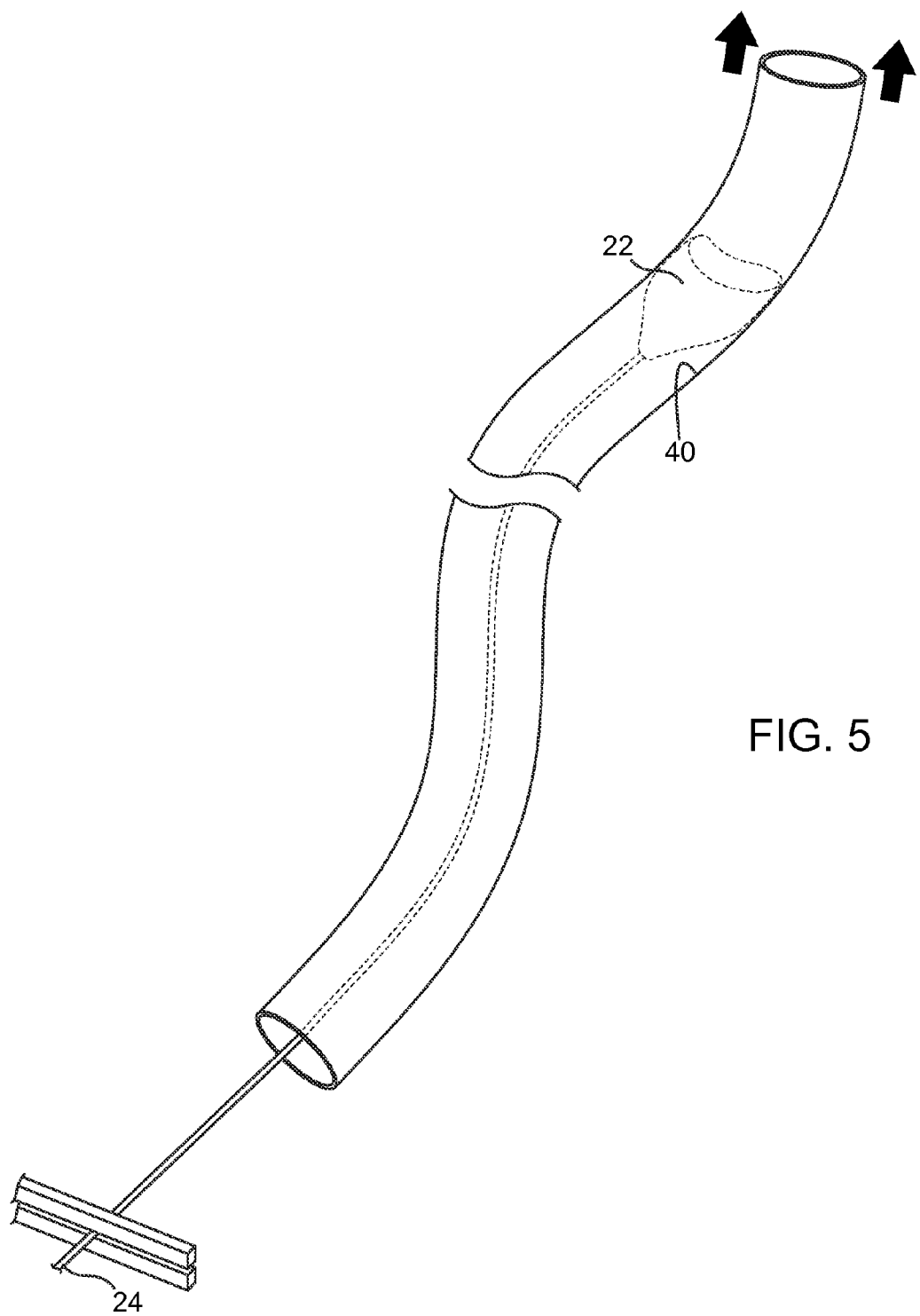

With particular reference to FIGS. 4 & 5, there is shown the method of use of the cleaning device in accordance with this invention. After assembly of the support member 24 and cleaning member 22, the distal end 32 of the support member 24 is inserted into one end of the tube 30. The distal end 32 is then affixed to a stationary household article, for example a dresser draw, which is first opened to allow the distal end 32 to be inserted into the drawer and then closed to secure the drawer with the distal end 32 affixed thereto.

Once so affixed, the support member 24 is in position to support the cleaning member 22 as the tube 30 is pulled over the cleaning member 22. The oversized cleaning member 22 brushes up against the interior walls 40. This operation can be repeated as often as required. It is suggested that each cleaning include a replacement of the cleaning member 22. However, depending upon usage and the amount of containments dislodged by the cleaning member 22, the same cleaning member 22 can be used for the different hoses connected with the same CPAP. However, it is strongly recommended that the cleaning member 30 be changed for each new CPAP.

Since the cleaning member 30 has a diameter greater than the largest tube to be cleaned connected with the CPAP apparatus, only one size cleaning member 30 is needed for the CPAP apparatus. In other words, the device 20 in accordance with the instant invention uses a single size cleaning member regardless of the make or model of the particular CPAP apparatus. And, each of the hoses of the CPAP apparatus can be cleaned with the same size cleaning element, despite the fact that there are different diameters for each of the hoses.

Figure 6:
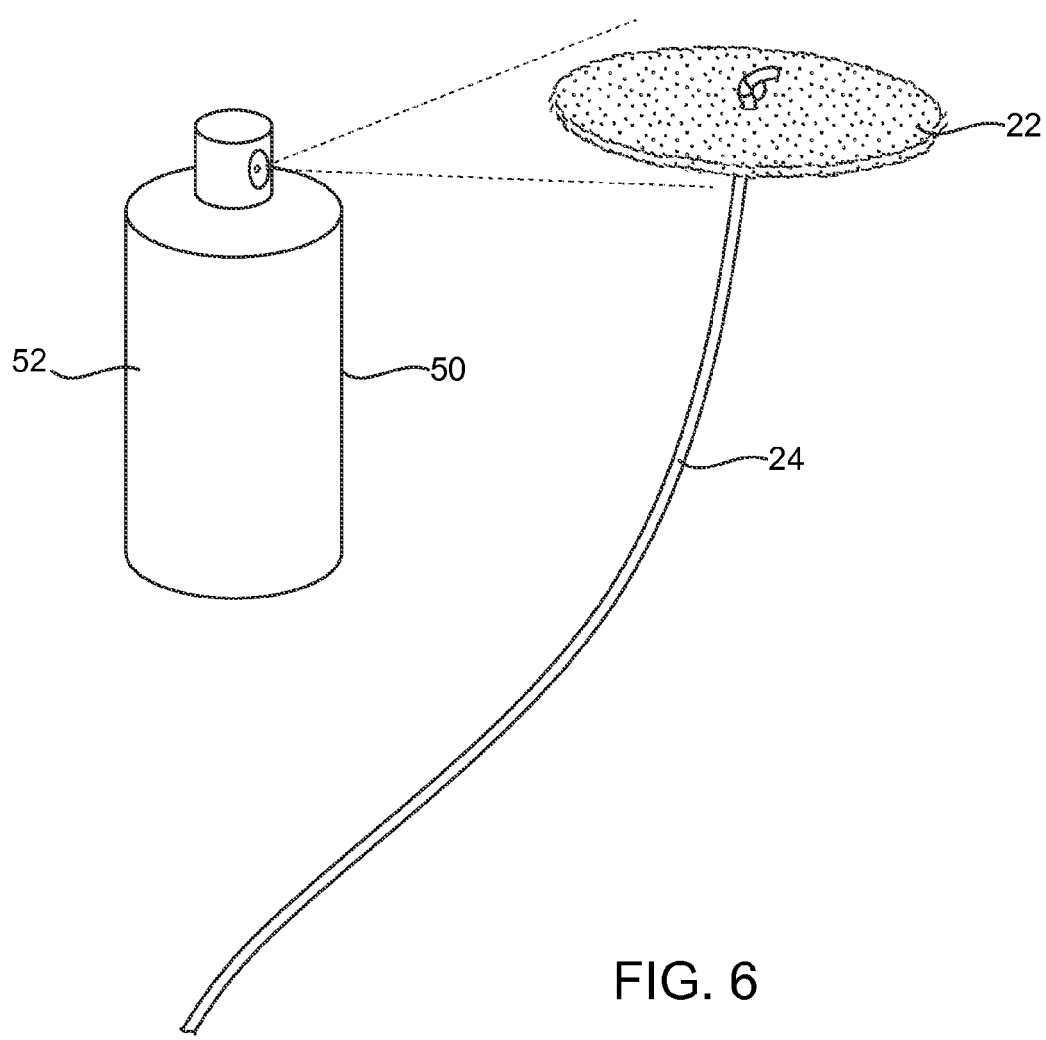
FIG. 6 illustrates an exemplary embodiment of the full kit of the cleaning device in accordance with this invention.

With particular reference to FIG. 6, there is shown an additional exemplary embodiment of the cleaning device and method in accordance with this invention. In this embodiment, the same elements including support member 24 and a cleaning member 22 are included. However, the device includes an additional member, namely a cleaning fluid 50. The cleaning fluid is sprayed onto the cleaning member 22 using an aerosol or pump sprayer 52. By slightly moistening the cleaning member 22, more containment is picked up by the cotton swab as the tube passes over it.

The cleaning fluid 50 may be of various types and may vary according to need. Accordingly, there is no best fluid to be provided. However, typically, the cleaning fluid has the composition of soap, vinegar and water solution in the ratio of one part soap, one part vinegar and twenty parts water. A low phosphoric soap is preferred so as to be less toxic to the environment. Of course, the cleaning fluid in accordance with the instant invention is non-toxic and safe as a cleaning fluid for human usage.

While the foregoing detailed description has described several embodiments of the method and cleaning device for cleaning an airway breathing hose in accordance with this invention, it is to be understood that the above description is illustrative only and not limiting of the disclosed invention. It will be appreciated there are variations of the support member, nylon works, but other material for the support member are also suitable. And, while the cleaning member is cotton herein, other various materials are similarly suitable for the purposes and functions of the method and device herein. It will be appreciated that the invention is fully disclosed in the exemplary embodiments discussed above and that there are numerous other embodiments that are not mentioned, but within the scope and spirit of this invention. Thus, the invention is to be limited only by the claims as set forth below.

What is claimed is:

1. A device for cleaning an airway hose, defining an open ended tube, the airway hose specifically adapted for attachment to a continuous positive airway apparatus, the device comprising:
   a cleaning element for cleaning the inside of the open ended tube, the cleaning element includes a central opening;
   a support member, the support member adapted for being threaded through the central opening of the cleaning element for attaching the cleaning element to the support member and for retaining the cleaning element to the support member during cleaning, defining a compound rope including at least some nylon and upon the application of heat to the first end, the first end is singed such that the first end defines an end sufficient for poking through a cotton swab and the second end being tied in a knot and upon the application of heat to the knot, the knot suitably strong enough so that the cleaning element is retained on the support member during cleaning.

2. A cleaning device as set forth in claim 1, wherein the cleaning element is replaceably attached to the support member.

3. A cleaning device as set forth in claim 2, wherein the cleaning element comprises a cotton swab having a central opening through which the support member is threaded.

4. A cleaning device as set forth in claim 1, wherein the support member defining a rope is a predetermined length and wherein that length is greater than the length of the open ended tube.

* * * * *